(12) United States Patent
Cular et al.

(10) Patent No.: US 8,089,196 B1
(45) Date of Patent: Jan. 3, 2012

(54) MICROCAVITY ENHANCED SURFACE ACOUSTIC WAVE DEVICES

(75) Inventors: Stefan Cular, Alexandria, VA (US); Venkat R. Bhethanabotla, Tampa, FL (US)

(73) Assignee: University of South Florida, Tampa, FL (US)

( * ) Notice: Subject to any disclaimer, the term of this patent is extended or adjusted under 35 U.S.C. 154(b) by 288 days.

(21) Appl. No.: 12/398,746

(22) Filed: Mar. 5, 2009

Related U.S. Application Data

(60) Provisional application No. 61/033,951, filed on Mar. 5, 2008.

(51) Int. Cl.
*H01L 41/04* (2006.01)
*H03H 9/25* (2006.01)
*H01L 23/00* (2006.01)

(52) U.S. Cl. .................................................. 310/313 R

(58) Field of Classification Search ............... 310/313
See application file for complete search history.

(56) References Cited

U.S. PATENT DOCUMENTS

| | | | | |
|---|---|---|---|---|
| 3,883,831 A | * | 5/1975 | Williamson et al. | 333/153 |
| 3,931,598 A | * | 1/1976 | Bongianni | 333/150 |
| 4,097,825 A | * | 6/1978 | Gerard | 333/151 |
| 4,155,056 A | * | 5/1979 | Cross et al. | 333/195 |
| 4,336,514 A | * | 6/1982 | Paige | 333/195 |
| 4,598,224 A | * | 7/1986 | Ballato | 310/313 R |
| 4,598,261 A | * | 7/1986 | Ballato | 333/195 |
| 4,634,914 A | * | 1/1987 | Ballato | 310/313 D |
| 7,027,921 B2 | | 4/2006 | Kalantar-Zadeh et al. | |
| 7,868,517 B2 | * | 1/2011 | Belot et al. | 310/313 R |

OTHER PUBLICATIONS

Bender, F., Dahint, R., and Josse, F. 1999. "Acoustic Wave-Based Sensors Using Mode Conversion in Periodic Gratings." IEEE Transactions on Ultrasonics, Ferroelectrics, and Frequency Control. vol. 46. No. 6. pp. 1497-1503.
Pastureaud, T., Lardat, R., Steichen, W., and Ventura, P. 2005. "Analysis of SAW Propagation Under a Periodic Multi-Electrode-Type Grating." IEEE Ultrasonics Symposium. pp. 683-686.
Becker, H., Von Schickfus, M. and Hunklinger, S. 1996. "A New Sensor Principle Based on the Reflection of Surface Acoustic Waves." Sensors and Actuators A. vol. 54. pp. 618-621.
Liu, Z., and de Boer, R. 1997. "Dispersion and Attenuation of Surface Waves in a Fluid-Saturated Porous Medium." Transport in Porous Media. vol. 29. pp. 207-223.
Dmitriev, V. F., and Mitrofanov, I. S. 1999. "Dispersion of SAW Velocity and Transformation of SAW into the Bulk Waves in Reflective Gratings." Joint Meeting EFTF-IEEE-IFCS.
Newton, M.I., McHale, G., and Martin, F. 2004. "Experimental Study of Love Wave Devices with Thick Guiding Layers." Sensors and Actuators A. vol. 109. pp. 180-185.

(Continued)

*Primary Examiner* — Jaydi San Martin
(74) *Attorney, Agent, or Firm* — Robert Varkonyi; Smith & Hopen, P.A.

(57) ABSTRACT

Shear-horizontal surface acoustic wave sensors with microcavities in the delay paths were studied using finite element methods. The microcavity devices are SAW delay path devices that have the delay path etched with square patterns at various wavelength dimensions and varying depths to increase the dispersion and bulk to surface wave conversion. Additionally the microcavities are filed with polystyrene to act as an inhomogeneous waveguide for further entrapment of wave energy near the device surface. The effects of microcavities and grooves on SAW propagation show significantly greater energy transmission than the other structures presented traditional sensors.

20 Claims, 12 Drawing Sheets

OTHER PUBLICATIONS

Ventura, P., ans Steichen, W. 2007. "FEM/BEM Analysis of a Generalized Periodic Array." IEEE Transactions on Ultrasonics, Ferroelectrics, and Frequency Control. vol. 54. No. 10. pp. 2052-2059.

Hofer, M., Finger, N., Kovacs, G., Zaglmayr, S., Langer, U., and Lerch, R. 2006. "Finite-Element Simulation of Wave Propagation in Periodic Piezoelectric Saw Structures." IEEE Transactions on Ultrasonics, Ferroelectrics, and Frequency Control. vol. 53. No. 6. pp. 1192-1201.

Gulyaev, Y. V., and Grigorievski, V. I. 2003. "Longitudinal Leaky Surface Acoustic Waves in Periodic Systems of Metal Electrodes on Lithium Niobate." IEEE Ultrasonics Symposium. pp. 2118-2121.

McHale, G., Martin, F. and Newton, M. I. 2002. "Mass Sensitivity of Acoustic Wave Devices from Group and Phase Velocity Measurements." Journal of Applied Physics. vol. 92. No. 6. pp. 3368-3373.

Makkonen, T., and Plessky, V. P. 2005. "Modeling Longitudinal Leaky Saw Propagation Under Periodic Electrode Arrays." IEEE Ultrasonics Symposium. pp. 691-694.

Pollard, T. B., and Pereira Da Cunha, M. 2006. "Pure Shear Horizontal SAW Network Model for Periodic Structures Including Bulk Scattering." IEEE Ultrasonics Symposium. pp. 88-91.

Huang, F. and Paige, E. G. S. 1982. "Reflection of Surface Acoustic Waves by Thin Metal Dots." Ultrasonics Symposium. pp. 72-82.

Kovacs, G. Lubking, G. W., Vellekoop, M. J. and Venema, A. 1992. "Love Waves for Biochemical Sensing in Liquids." Ultrasonics Symposium. pp. 281-285.

Yantchev, V. M. and Strashilov, V. L. 2002. "Surface Transverse Waves in Polymer-Coated Grating Configurations." Journal of Applied Science. vol. 91. No. 9. pp. 5700-5705.

Turton, A. C., Bhattacharyya, D., and Wood, D. 2005. "High Sensitivity Love-Mode Liquid Density Sensors." Sensors and Actuators A. vol. 123-124. pp. 267-273.

Renard, A., Henaff, J., and Auld, B. A. 1981. "SH Surface Wave Propagation on Corrugated Surfaces of Rotated Y-Cut Quartz and Berlinite Crystals." Ultrasonics Symposium. pp. 123-128.

Bender, F., Dahint, R., and Josse, F. 1999. "Surface Acoustic Wave-Based Sensors Using Mode Conversion in an Array of Periodic Gratings." Joint Meeting EFTF-IEEE IFCS. pp. 973-977.

Sandia Corporation. 2010. "Microsensors and Sensor Microsystems." http://sandia.gov/mstc/MsensorSensorMsystems/technical-information/SH-SAW-bio... accessed Jun. 30, 2011.

* cited by examiner

Before streaming

After streaming

MICROCAVITY ENHANCED SURFACE ACOUSTIC WAVE DEVICES

CROSS REFERENCE TO RELATED APPLICATION

This application claims priority to pending U.S. Provisional Patent Application No. 61/033,951, entitled "Microcavity Enhanced Surface Acoustic Wave Devices", filed on Mar. 5, 2008, the contents of which are herein incorporated by reference.

STATEMENT OF GOVERNMENT INTEREST

This invention was made with Government support under Grant No. DGE-0221681 awarded by the National Science Foundation and Grant No. W81XWH-05-1-0585 awarded by the United States Army Medical Research Acquisition Activity. The federal government has certain rights in this invention.

FIELD OF INVENTION

This invention relates to surface acoustic wave (SAW) devices. More specifically, the invention presents novel SAW devices with decreased power consumption and a concurrent increase in sensitivity of the device.

BACKGROUND OF THE INVENTION

Thickness Shear Mode Resonator (TSM) or quartz crystal microbalance (QCM), is the oldest and simplest acoustic wave device, with good durability in harsh environments. A TSM usually comprises a thin disk of AT-cut quartz with parallel circular electrodes patterned on both sides. Running a voltage between the two electrodes results in a shear deformation of the crystal, causing the crystal to resonate as electromechanical standing waves are created. Wave displacement is maximized at the crystal faces, making the device sensitive to surface interactions. Typical TSM resonators operate between 5 and 30 MHz.

Surface Acoustic Wave (SAW) devices use waves with a longitudinal and a vertical shear component with virtually all their acoustic energy confined within one wavelength of a substrate's surface. These components can couple with a medium in contact with the substrate, as seen in FIG. 1, which strongly affects the amplitude and velocity of the wave and allows SAW sensors to directly sense mass and mechanical properties. SAW velocities are approximately 5 orders of magnitude less than the corresponding electromagnetic (bulk) wave, making SAWs among the slowest to propagate in solids. Typical SAW sensors operate from 25 to 500 MHz.

As it is known in the art, SAW devices are employed in a variety of applications, such as resonators and delay lines for oscillator circuits, filters and pressure transducers. Generally, a SAW device comprises at least one transducer including a set of conductive members which is disposed on or recessed within a surface of a piezoelectric substrate. One disadvantage of these devices is that Rayleigh mode SAWs have surface-normal wave components, seen in FIG. 2, making them poorly suited for liquid sensing, as the longitudinal waves caused by contact with a liquid excessively attenuate the surface wave.

In many applications of SAW devices, particularly with respect to applications of resonators and delay lines, as frequency stabilizing and determining elements in oscillators, it is important to provide a package having a relatively small size while, at the same time, properly mounting the SAW device within the package to reduce the so-called vibration sensitivity of the SAW device. SAW devices were originally used for electronic filtering of high frequency waves. Due to the nature of the waves, SAW devices became important as sensors, and may be used for biosensors and chemical sensors, and communication surface acoustic wave filters. SAW sensors may effectively detect trace amounts of chemical in a solution. A class of shear horizontal waves, Love-waves, are propagated in layered devices that concentrate the wave energy in a highly confined region near the surface. However, the sensors are limited by power consumption and reproducibility. As such, new SAW devices are needed for applications such as improvised explosive device discovery to diagnostic personal health care.

SUMMARY OF THE INVENTION

SAW devices can be integrated with common electronics, enabling a high level of sensitivity in those devices. Advantageously, SAW devices are capable of manipulating sensing films and permit the circulation of fluids near the sensor surface. Shear-horizontal surface acoustic wave devices with micro-cavities in the delay paths of 36° YX—$LiTaO_3$ substrate were studied using finite element methods. The devices include a piezoelectric substrate with a plurality of inter-digitated transducers disposed on a face of the substrate. An array comprising a plurality of micro-cavities are disposed on the face of the substrate within the wavepath of the SAW. The micro-cavities may be circular, triangular, pentagonal, or square in cross-section. The micro-cavities have dimensions determined by wavelengths of the propagating SAW or fractions thereof. In some embodiments, the micro-cavities are $\lambda/2$, $\lambda/4$, or $\lambda/8$ in size, and optionally have set depths of $\lambda/2$, $\lambda/4$, and $\lambda/8$. The micro-cavities are disposed to constructively build the propagating SAW, and optionally located in the middle of the delay path where the highest amplitude acoustic waves are located. In certain embodiments, twenty micro-cavities are disposed on the face of the substrate micro-cavities, and may be disposed in an array of 4 rows of 5 micro-cavities.

The substrate used may be any piezoelectric known, such as quartz, R-plane sapphire, lithium niobate, lithium tantalate, gallium arsenide (GaAs), silicon carbide (SiC), langasite (LGS), zinc oxide (ZnO), aluminum nitride (AlN), lead zirconium titanate (PZT), and polyvinylidene fluoride (PVdF). In specific embodiments, the substrate is 36° YX $LiTaO_3$. Simulation results for non-filled and polystyrene-filled micro-cavity devices were compared with standard delay line shear-horizontal SAW, optimized Love-wave, and etched grating sensors. The best micro-cavities studied reduce insertion loss by 19.25 dB from 33.28 dB and exhibit velocity sensitivity 4.83 times larger than that of the standard SAW sensor simulated. In specific embodiments, the micro-cavities of the device are filled with a waveguide material with lower density and lower acoustic velocity than the substrate, such as polystyrene.

Challenges for developing sensors include factors such as sensitivity, power consumption and reproducibility. For surface acoustic wave (SAW) sensors, sensitivity is one of the most critical parameters and is often improved by decreasing the operational wavelength (D. Ballantine, et al., *Acoustic wave sensors: theory, design, and physicochemical applications*. (Academic Press, San Diego, 1997), pp. xii, 436). Sensitivity can also be improved through the addition of a guiding layer to create Love-wave devices (G. Kovacs, et al., "A Love wave sensor for (bio)chemical sensing in liquids," Seas.

Actuators, A 43(1-3), 38-43 (1994); G. McHale, et al., "Theoretical mass sensitivity of Love wave and layer guided acoustic plate mode sensors.," J. Appl. Phys 91(12), 9701-9710. (2002)). An analytical model solution by McHale et al. showed a theoretical improvement limit in sensitivity of 20 times for an optimized guiding layer thickness (G. McHale, et al., "Theoretical mass sensitivity of Love wave and layer guided acoustic plate mode sensors," J. Appl. Phys 91(12), 9701-9710. (2002)). Finite element (FE) simulations of the present invention show an improvement of 5.36 times the velocity sensitivity of the Love-wave sensor over a standard SAW sensor.

Also disclosed are methods for increasing surface acoustic wave (SAW) sensor sensitivity and decreasing surface acoustic wave (SAW) sensor power requirements. Etching an array comprising a plurality of micro-cavities on the face of the piezoelectric substrate is found to advantageously increase sensitivity of SAW devices. Furthermore, the use of the micro-cavities decreases power requirements for SAW devices. While various shapes were analyzed, it was found that square micro-cavities exhibited this unique characteristic. In specific embodiments, the micro-cavities have x-y dimensions selected from the group consisting of $\lambda/2 \times \lambda/2$, $\lambda/4 \times \lambda/4$, and $\lambda/8 \times \lambda/8$. The micro-cavities have a z-dimension selected from the group consisting of $\lambda/2$, $\lambda/4$, and $\lambda/8$.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Disclosed are shear-horizontal surface acoustic wave (SH-SAW) devices. Shear-horizontal surface acoustic wave sensors with micro-cavities of various shapes etched in the delay paths of 36° YX—LiTaO$_3$ substrate were studied using finite element methods. Micro-cavities with square cross-sections were found most beneficial, with optimal sizes $\lambda/4$ and $\lambda/2$, and of different depths were located in the middle of the delay path. Micro-cavities were either non-filled or polystyrene-filled to affect the reflection characteristics of the micro-cavities. The micro-cavity devices were then compared against standard delay line shear-horizontal SAW, optimized Love-wave, and etched grating sensors. The microcavity devices are SAW delay path devices that have the delay path etched with square patterns of $\lambda/2$, $\lambda/4$, and $\lambda/8$ dimensions at varying depths to increase the dispersion and bulk to surface wave conversion. Additionally the microcavities are filed with polystyrene to act as an inhomogeneous waveguide for further entrapment of wave energy near the device surface. The best micro-cavities studied reduce insertion loss by 19.25 dB from 33.28 dB and exhibit velocity sensitivity 4.83 times larger than that of the standard SAW sensor simulated. The effects of micro-cavities and grooves on SAW propagation for sensor applications are illustrated using finite element methods. The device and sensor effects of filling these micro-cavities and grooves with polystyrene, which is less dense and possesses lower acoustic velocity than the piezoelectric substrate, were analyzed.

The term "micro-cavity" or "microcavity" is used to refer to a void within the piezoelectric material, such an opening of any desired cavity. The micro-cavities are fractions of an analytic wavelength in dimension, such as $\lambda/2$. As used herein, an analytic wavelength is the distance between repeating units of a propagating surface wave designed for use in the piezoelectric material, without regard to whether the piezoelectric material is sued as a sensor or other device, such as an oscillator.

Figure 1:
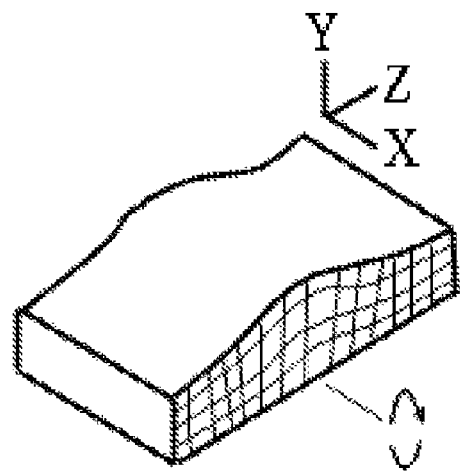
FIG. 1 is a diagram depicting a surface acoustic wave (SAW) moving in a direction normal to the surface plane of a SAW device. The motion of particles within the SAW flow in an elliptical Y and Z path, as depicted in the inlay.
Figure 2:
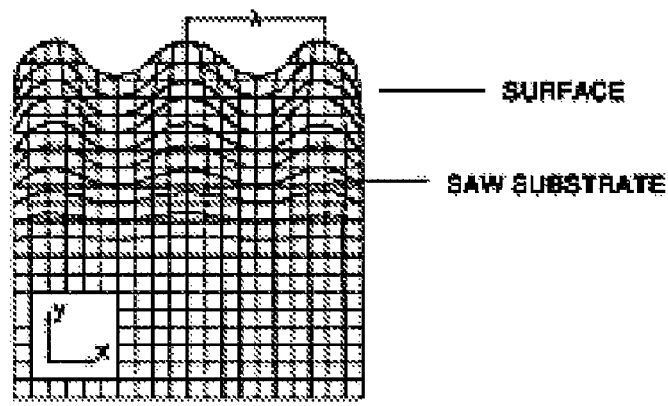
FIG. 2 is a diagram depicting the wave energy is confined to within one wavelength from the surface of a SAW sensor. This characteristic yields a sensor that is very sensitive to interactions with the surface.
Figure 2:
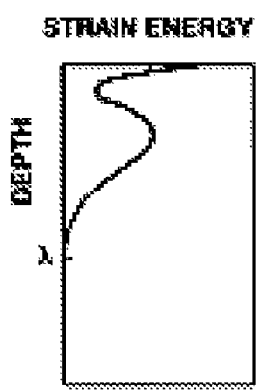
Figure 3:
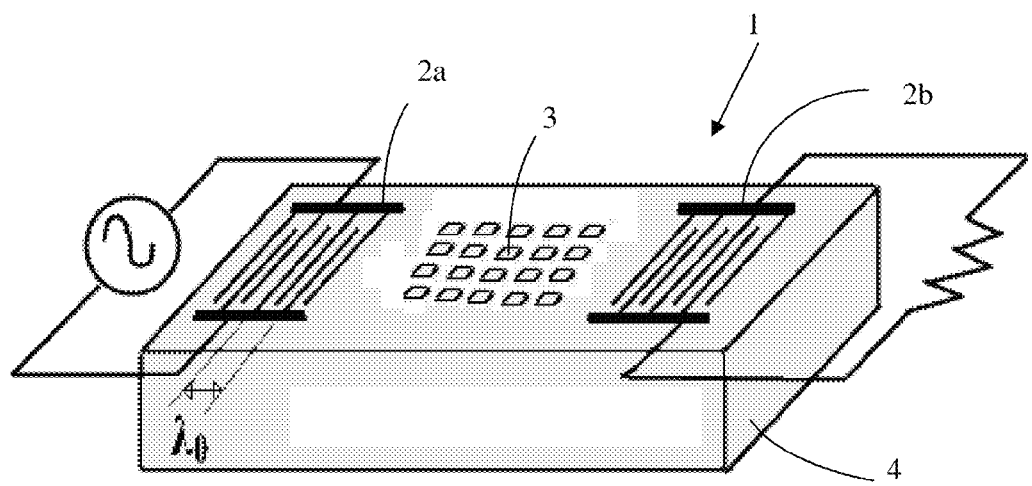
FIG. 3 is a diagram of a piezoelectric substrate of the present invention.

The surface acoustic wave device 1 comprises a piezoelectric substrate 4, which is selected and cut for a particular wave motion and wave properties, as seen in FIG. 3. Useful examples are substrates formed from a crystalline dielectric member, which may be prepared from quartz or any known piezoelectric. Other exemplary substrates are lithium niobate and lithium tantalate.

Interdigital transducers (IDT) 2 are deposited on a wave generating face of the substrate. The IDTs are typically metal, such as aluminum or gold. The dimensions of the IDT control the characteristics of the surface wave and typically designed in $\lambda/4$ and $\lambda/8$ widths, such that an electrical signal, like an AC signal, generates surface waves at input IDT 2a, which are received at sensing IDT 2b, seen in FIG. 4. An array of micro-cavities 3 are disposed in the wavepath between input IDT 2a and sensing IDT 2b, thereby altering the waves traveling through substrate 4, as seen in FIG. 5. Filling micro-cavities 3 with an acoustic medium 5 further permits alteration of the waves.

Power consumption is an important issue for sensors with increasing demand for personal and remote sensing applications. Ideal SAW delay line sensors have insertion loss of about 7 dB, and it is not uncommon to work with insertion losses of 20 dB. The simulated devices exhibit insertion losses ranged from 14.03 dB to 33.28 dB. This difference of loss between typical physical devices and simulated ones is primarily a result of the fewer interdigital transducer finger pairs utilized in simulation, and is for computational resource reasons. These differences will not affect the conclusions of the analysis. Common methods of decreasing insertion loss in SAW devices, not particularly sensors, include utilization of reflective gratings (D. Morgan, *Surface-Wave Devices for Signal Processing.* (Elsevier, New York, 1991)), grooves and corrugated gratings (R. Humphryes and E. Ash, "Acoustic Bulk-Surface-Wave Transducer," Electronic Letters 5 (9), 175-176 (1969); D. Chen, et al., presented at the 1982 Ultrasonics Symposium, 1982 (unpublished); C. Campbell, *Surface acoustic wave devices and their signal processing applications.* (Academic Press, Boston, 1989), pp. xiv, 470), and wave-guides (E. Gizehi, et al., "Detection of Supported Lipid Layers with the Acoustic Love Waveguide Device: Application to Biosensors," Sensors and Actuators B 34, 295-300 (1996)). The recurring concepts in these four primary methods to reduce the SAW device power loss are the conversion bulk waves into surface waves, and entrapment of energy near the surface that would otherwise be lost to bulk waves (D. Morgan, *Surface-Wave Devices for Signal Processing.* (Elsevier, New York, 1991); B. A. Auld, *Acoustic fields and waves in solids.* (Wiley, New York, 1973), p. 2 v).

Figure 4:
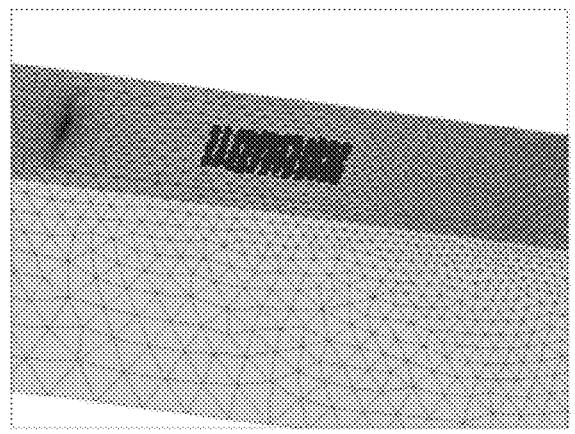
FIG. 4 is a pre-solution three-dimensional split finger IDT design with highest mesh density loaded at the center of the delay path, seen on the right side of image.
Figure 5:
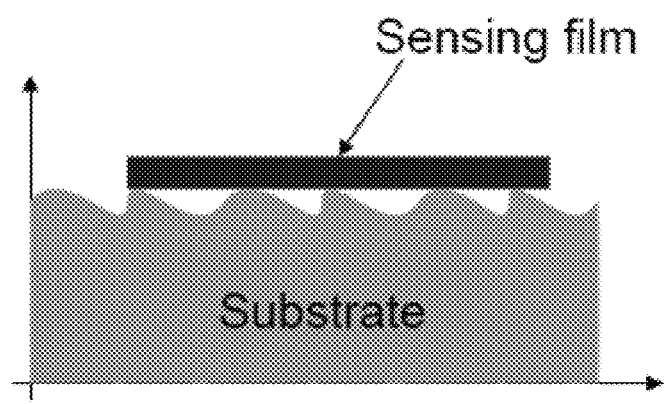
FIG. 5 is an illustration of AC-generated surface waves propagating through the piezoelectric substrate to the sensing layer.
Figure 6:
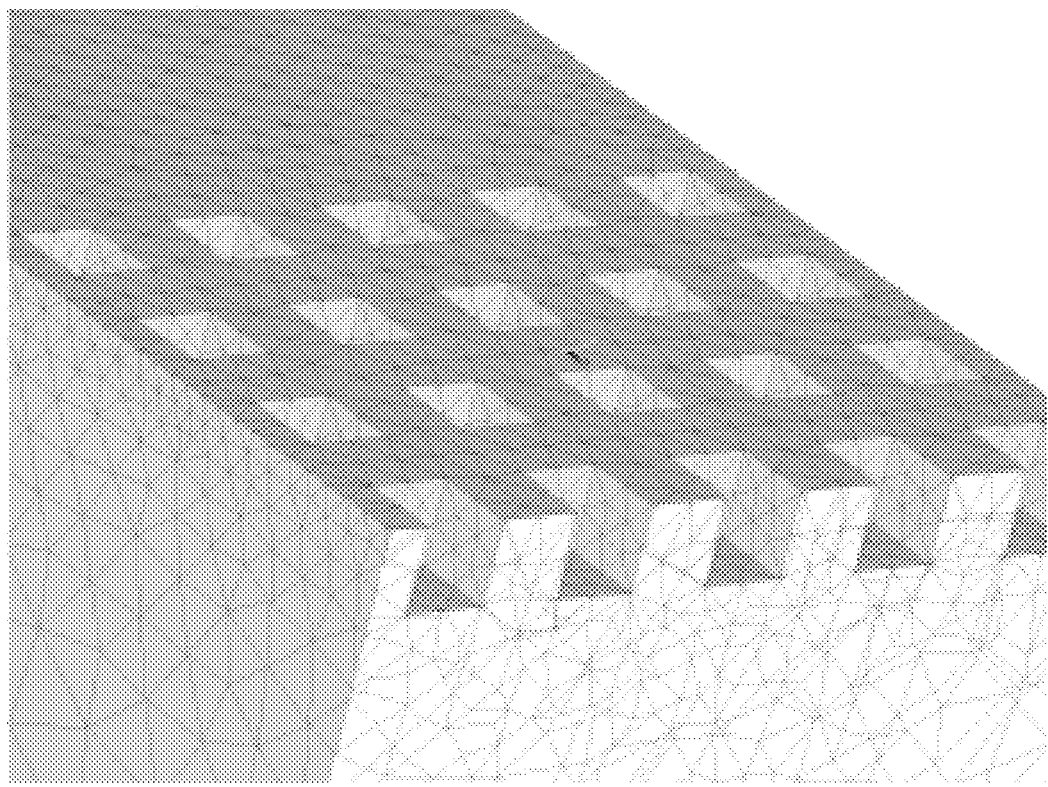
FIG. 6 is a cross-section of meshed $\lambda/2 \times \lambda/2 \times \lambda/2$ microcavity SAW device.

A simulation of the SAW device 1, seen in FIGS. 4 and 6, was performed with three dimensional FE models created in ANSYS. Transient response of the SAW device to an impulse input applied at the transmitting inter-digitated transducer (IDT) fingers was utilized to study the wave generation and propagation characteristics as well as to deduce its frequency response. The models were designed using a 36° YX LiTaO$_3$ substrate which is 40λ long, 5λ wide and 5λ deep (200 μm×1,600 μm×200 μm), with IDTs that are 2λ long and λ/4 wide with a periodicity of 40 μm. For this work, the transducers were considered to be mass-less elements with six finger pairs. No metallization was used. Tetrahedral elements, of about 230,000 nodes, seen in FIGS. 4 and 6, were used throughout the model with 4 degrees of freedom to account for voltage and particle displacements in the x-, y- and z-directions. Elements were formed to ensure highest density on the top center surface of the substrate where the most deformation occurs. The simulations were initiated with an electric impulse of 10 V applied at the transmitting IDT fingers with time steps of 0.95 ns. The simulation was carried out for 190 ns and parabolic fitting/interpolation between the 0.95 ns time-steps were used on all data. The simulation time and dimensions for the models were chosen to prevent reflected signals from the ends and bottom of the substrate.

The micro-cavity devices were developed by combining etched substrates with square patterns of λ/2, λ/4 and λ/8 dimensions at varying depths between 0 and 3.0 μm in the substrate and along the wave path. These micro-cavities were designed to increase the dispersion and bulk to surface wave energy conversion. The models were so configured that 20 identical micro-cavities were located in the middle of the delay path forming 4 rows of 5 micro-cavities each as shown in the cross-section of the meshed model in FIG. 6.

These devices were studied in comparison to etched gratings. For comparison, grooves (etched gratings) of length λ/4 and λ/2 with width equivalent to the aperture of the IDTs and depths the same as the cavities were simulated. The micro-cavities were then filled with polystyrene to produce an inhomogeneous waveguide for additional entrapment of the wave energy near the device surface. However any material with a lower density and lower acoustic velocity than the substrate is envisioned. The device design that gave the best characteristics was utilized to measure sensitivity by application of an ideal mass. The same mass was added to a standard SAW sensor, an optimized Love-wave sensor, and an etched grating sensor for comparison using a combined sensitivity term that accounts for both voltage and velocity perturbations.

Figure 7:
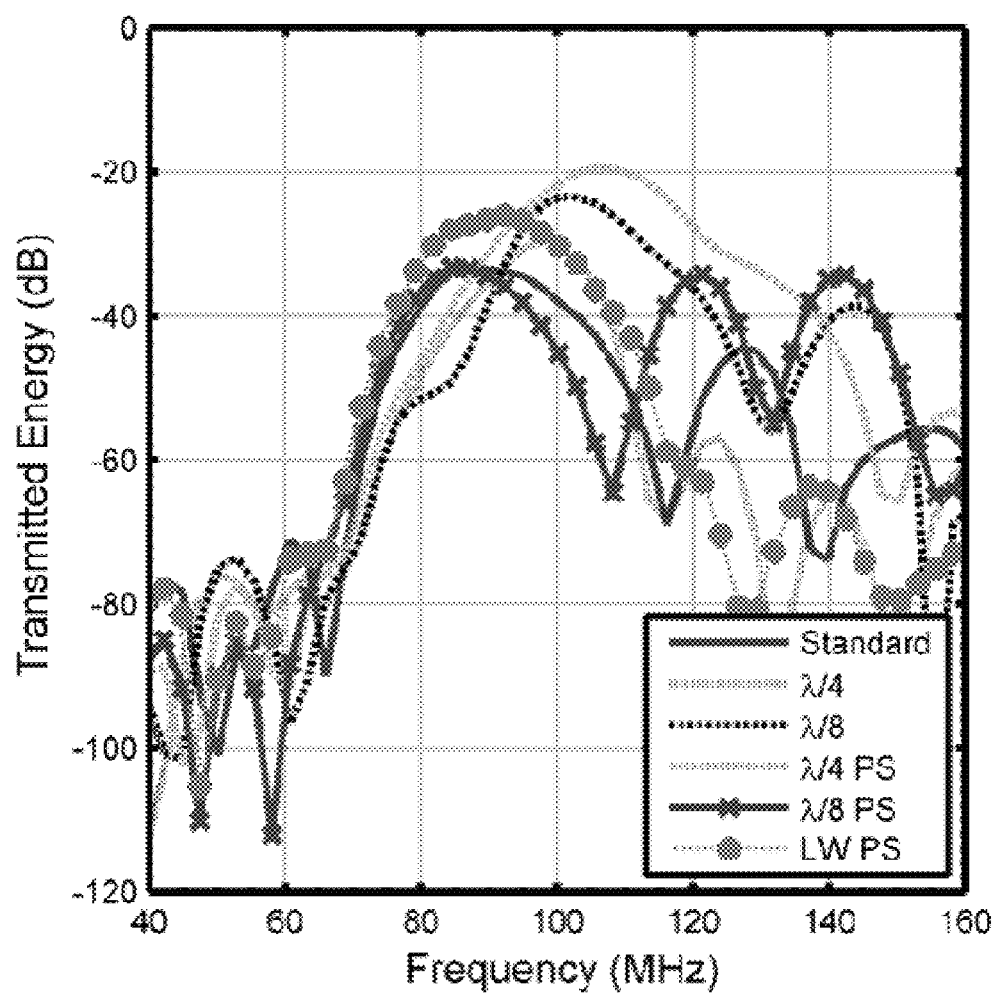
FIG. 7 is a graph comparing transmitted energies for the polystyrene-filled and unfilled devices with micro-cavities of $\lambda/4$ square cross-section and depths of $\lambda/4$ and $\lambda/8$, an optimized Love-wave device, and a standard SAW delay line device.
Figure 8:
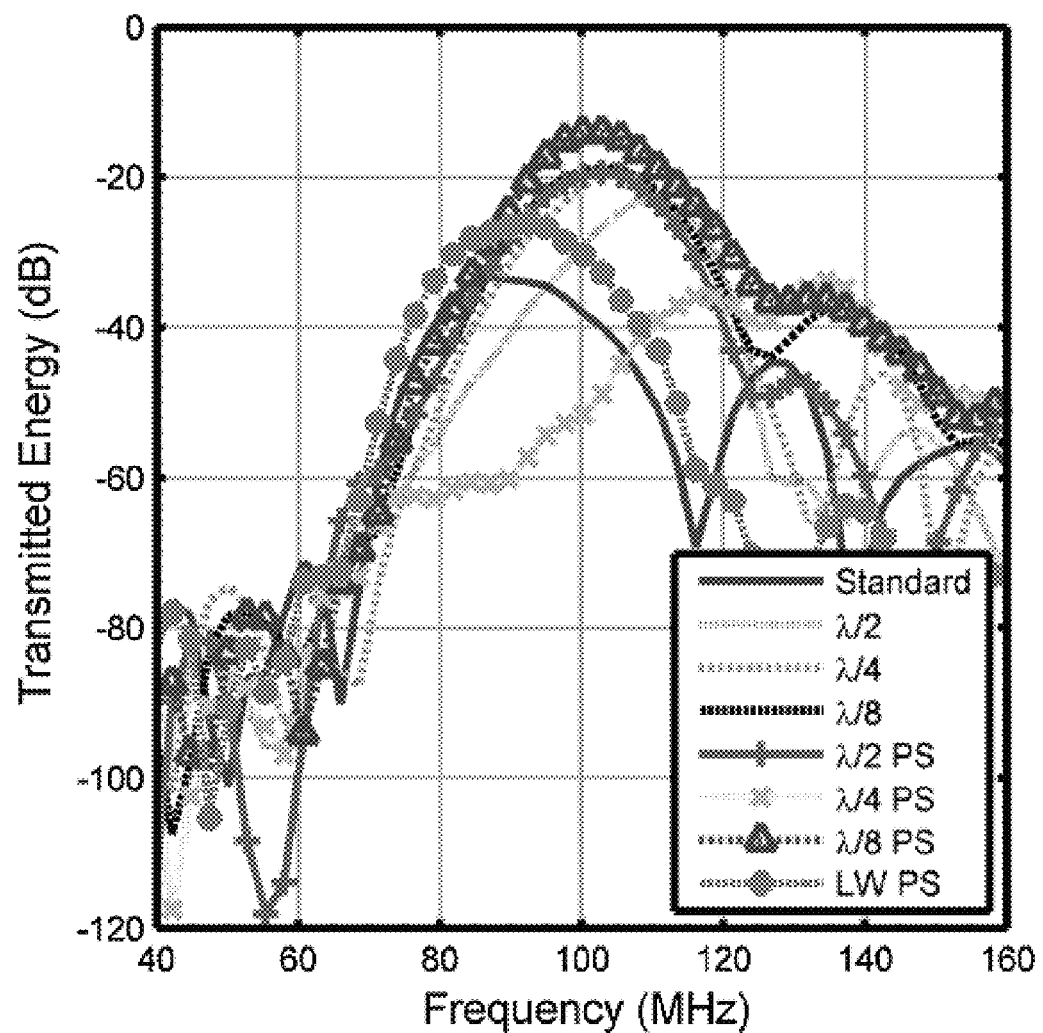
FIG. 8 is a graph comparing transmitted energies for the polystyrene-filled and unfilled devices with micro-cavities of $\lambda/2$ square cross-section and depths of $\lambda/2$, $\lambda/4$ and $\lambda/8$, an optimized Love-wave device, and a standard SAW delay line device.

Transmitted energies across the band pass for the λ/4 designs are shown in FIG. 7, and for the λ/2 designs in FIG. 8. The best of the λ/4 designs with λ/4 depth micro-cavities filled with PS shows 14.26 dB larger energy transmission across the delay path compared to a plain path. This design also shows significant improvement over the Love-wave (LW) design, seen at 6.66 dB. Notably, the λ/8 depth non-filled device shows transmission behavior between the λ/4 depth PS-filled and the LW designs. Data taken for the λ/2 designs indicate micro-cavities set at the λ/8 depth and filled with PS exhibit a 5.35 dB improvement over the best λ/4 design, i.e., the λ/4 cubic micro-cavity filled with PS, as seen in FIG. 8. The etched gratings (data not shown in figures for clarity) non-filled and PS-filled have insertion losses ranging from 15.9 dB to >33.0 dB.

Figure 9:
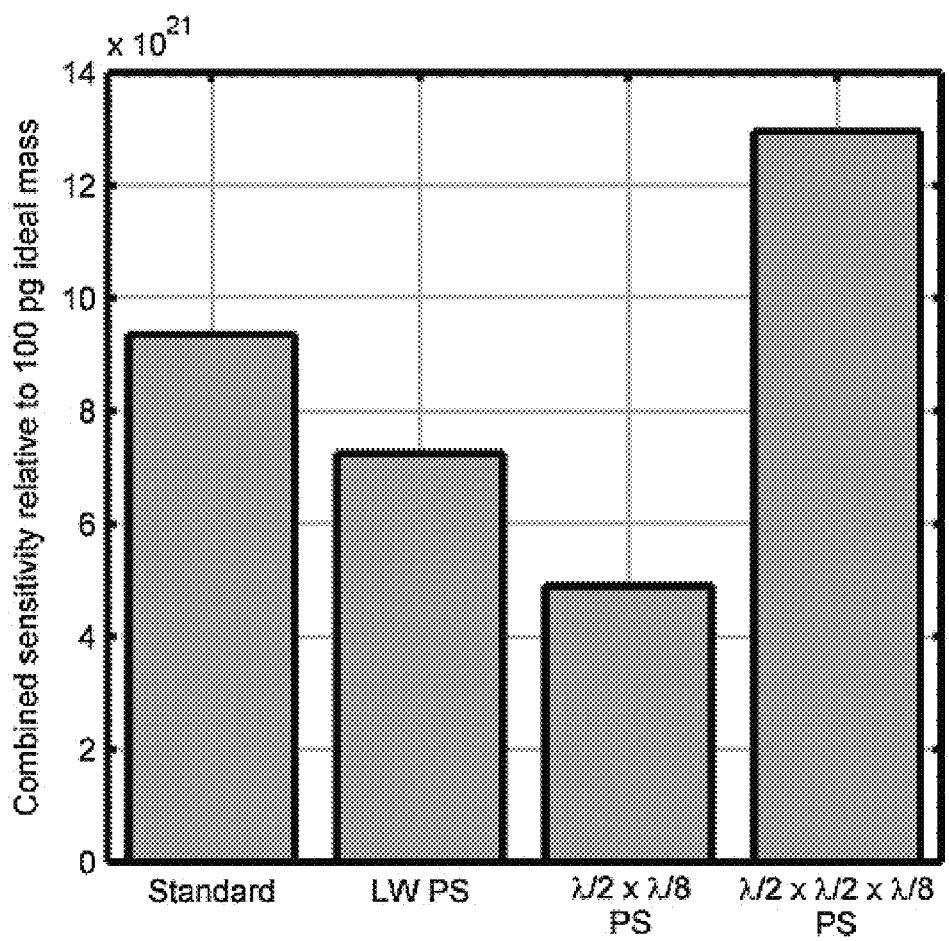
FIG. 9 is a bar graph comparing the combined velocity and voltage mass sensitivities of a plain single split finger SAW sensor, an optimized 2,200 nm polystyrene Love-wave sensor, a $\lambda/2$ length by $\lambda/8$ depth groove grating filled with polystyrene, and a $\lambda/2$ length by $\lambda/2$ width by $\lambda/8$ depth micro-cavity array filled with polystyrene.
Figure 10:
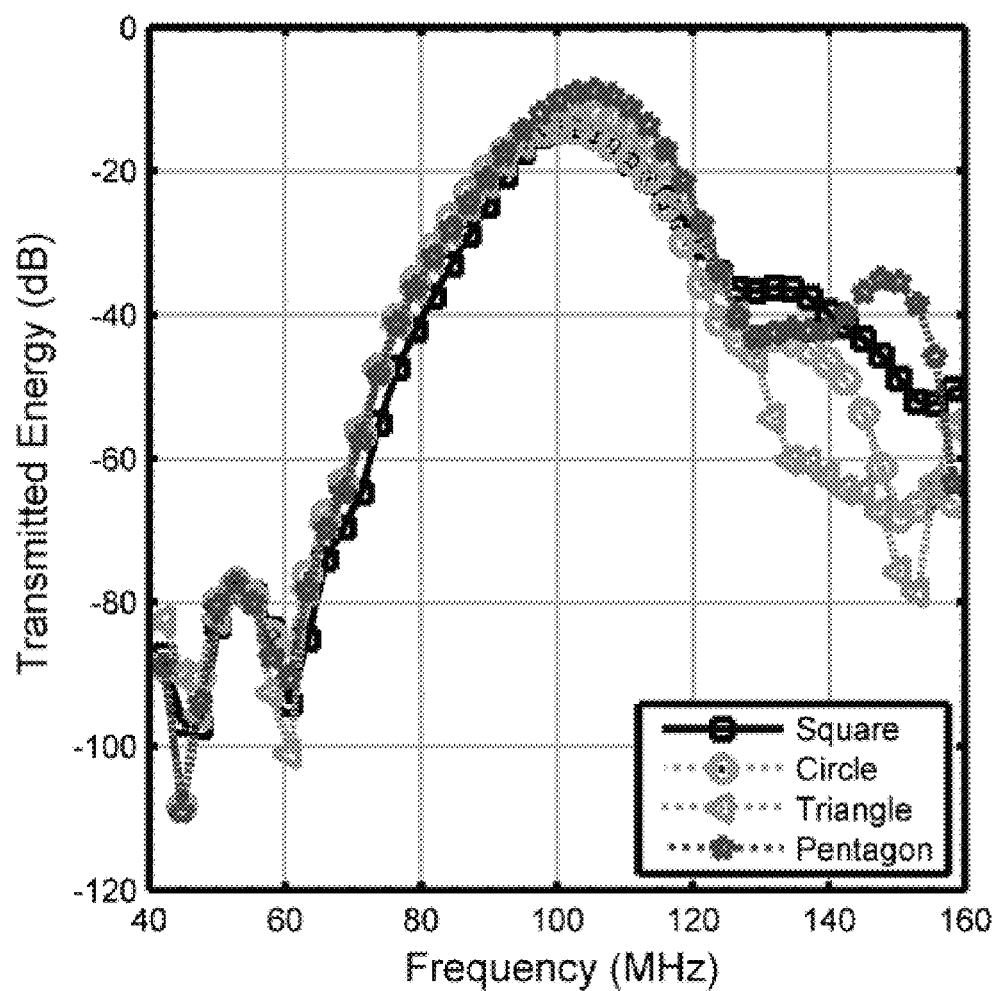
FIG. 10 is a graph comparing transmitted energies for micro-cavities of varying shapes.
Figure 11:
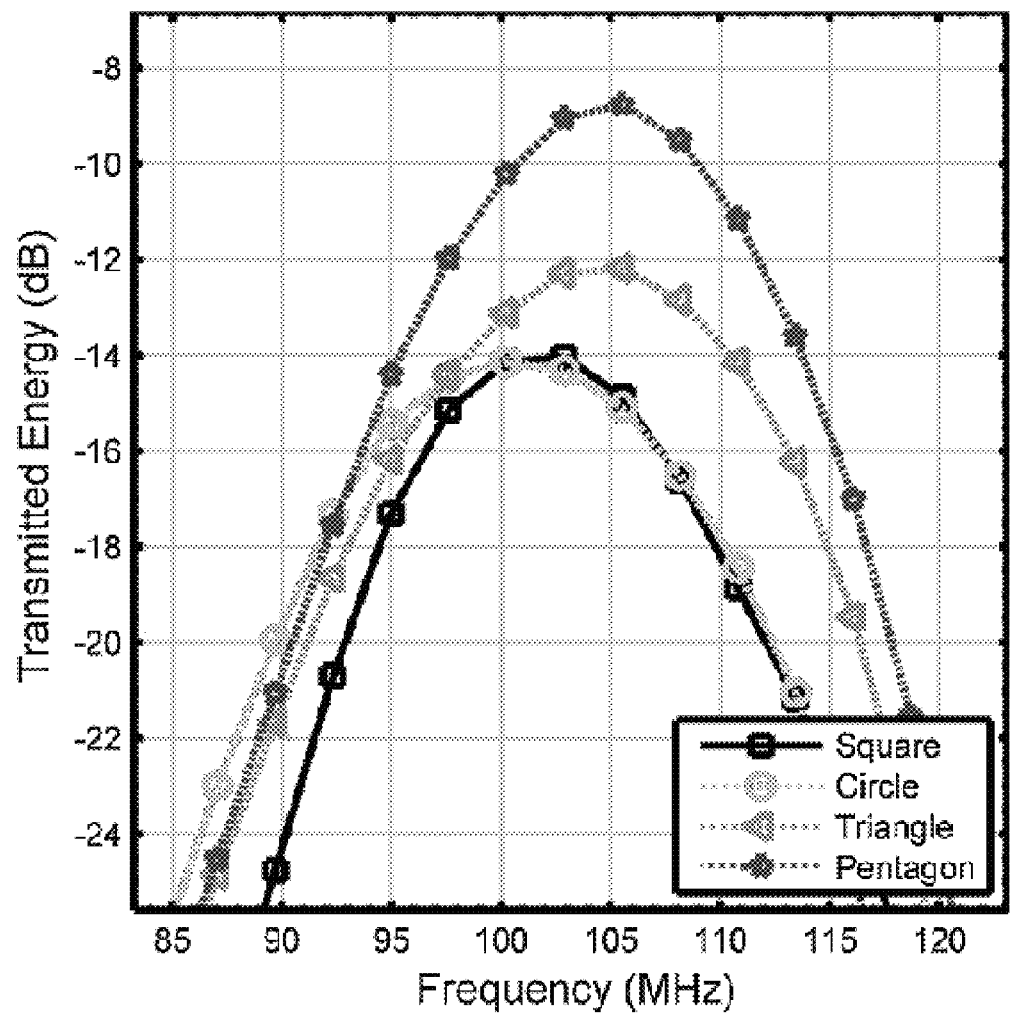
FIG. 11 is a graph comparing transmitted energies for micro-cavities of varying shapes.
Figure 12:
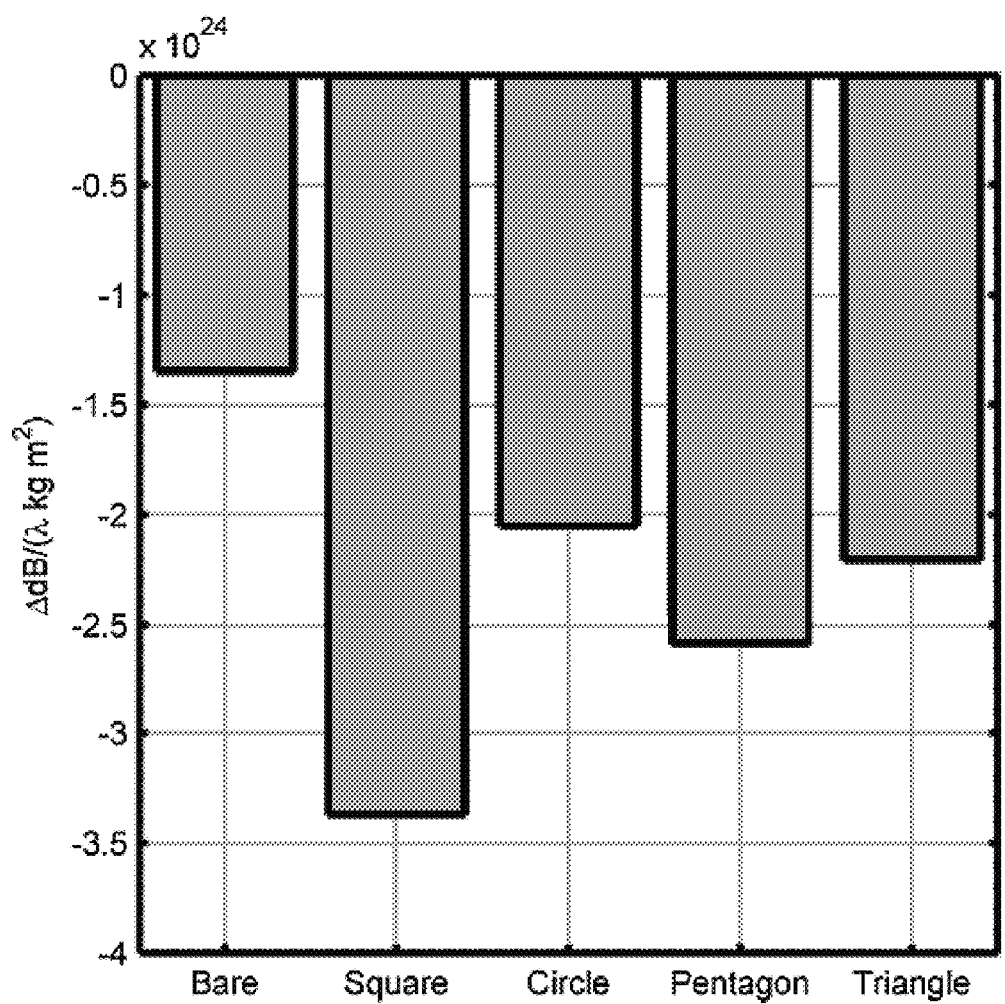
FIG. 12 is a bar graph comparing the micro-cavity shape to mass sensitivity for a 100 pg mass applied to $9.6 \times 10^{-5}$ cm$^2$.

The λ/2 width by λ/2 length by λ/8 depth PS-filled micro-cavity also showed the greatest energy transmission across the delay path and was chosen for comparison to a standard split finger sensor, Love-wave sensor, and λ/2 width by λ/8 depth groove grating PS-filled sensor, using sensitivity measures. Simulation models were created to apply a 100 pg mass across 9,600 μm$^2$ center in the delay path of the SAW sensor. The same transient analysis utilized for studying transmission characteristics was performed on these ideal-mass-perturbed sensors using test masses at 1, 10, 100, and 1000 pg applied to the 9.6×10$^{-5}$ cm$^2$ sensors and the square root of the summation of the squares of velocity and voltage taken to identify the combined sensitivity. The resulting data, seen in FIG. 9, indicate the λ/2×λ/2×λ/8 PS-filled micro-cavity device was most sensitive to perturbations. Utilizing this sensitivity measure, the data show the device with the λ/2×λ/2×λ/8 micro-cavity array filled with polystyrene to be 1.38 times more sensitive than a standard split finger SAW sensor and 1.79 times more sensitive than an optimized Love-wave SAW sensor. It was also noted that the shape of the micro-cavity impacts the characteristics of the transmitted energy across the bandpass, seen in FIGS. 10 and 11. Square-shaped micro-cavities were found the most sensitive to mass perturbations, as seen in FIG. 12, indicating this design transmits more energy on the surface of the device. Although the finite element models simulated in this work are limited in comparison to experimental dimensions, recent studies show that the results indicate clear trends that are found in experimental studies (S. Sankaranarayanan, et al., "Flow induced by acoustic streaming on surface-acoustic wave devices and its application in biofouling removal: A computations study and comparisons to experiment," Physical Review—E 77(6), 66308, (2008)).

Figure 13:
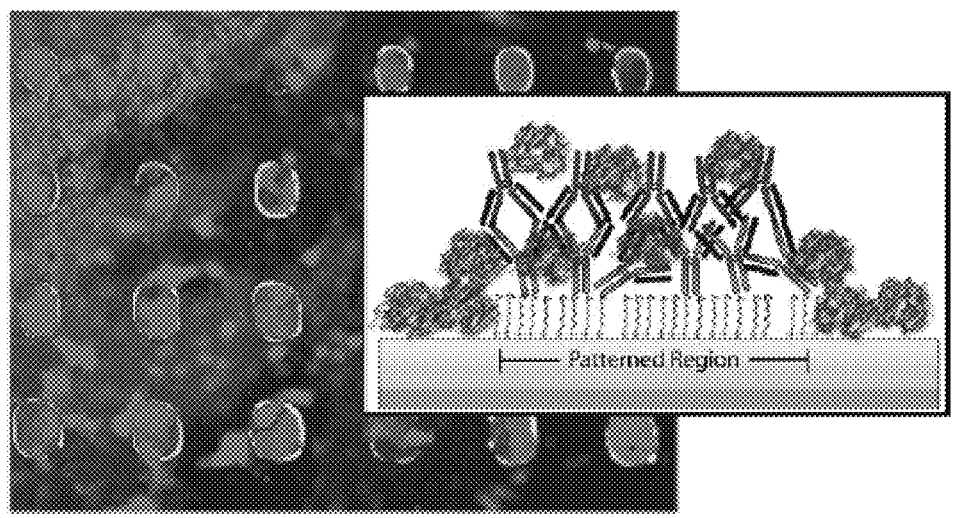
FIGS. 13(a) and (b) are images showing acoustic streaming of sensors. The inlays are diagrams illustrating the effects seen in the images.
Figure 13:
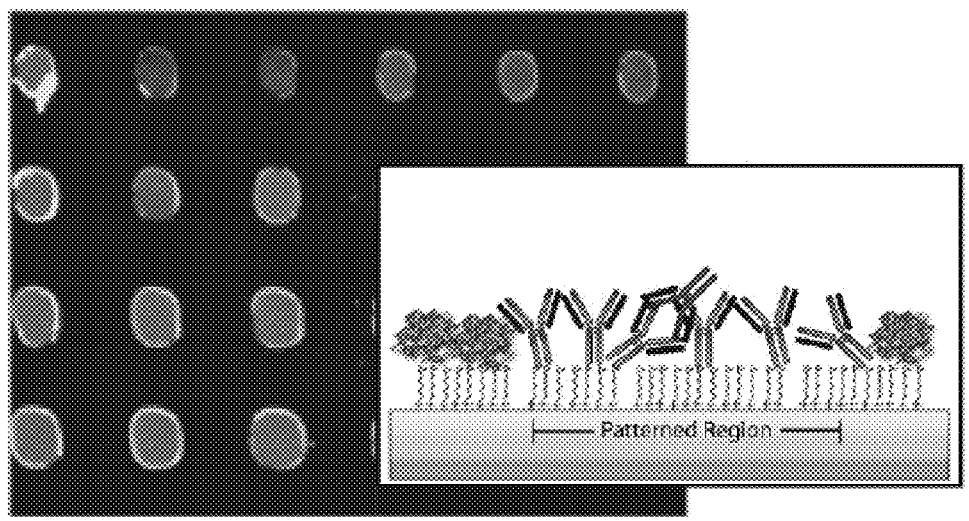

A major concern for sensor reliability involves fouling. In biological testing, binding of non-specific proteins to the sensor surface results in fouling, seen in FIG. 13(*a*), which limits reuse of the sensor and negatively affects sensor response. It was recently found that fluid motion induced by high intensity sound waves, known as acoustic streaming, is useful in removing interfering agents, as seen in FIG. 13(b).

Ideal sensors exhibit wave motions that are closely confined to the substrate surface, such as shear horizontal-surface acoustic waves (SH-SAW). The different devices tested—a standard SAW sensor, an best etched grating sensor, a micro-cavity SAW sensor, and PS-micro-cavity device-showed different wave motions, with the micro-cavity devices exhibiting more surface confined waves.

Filling the micro-cavities and grooves with polystyrene (PS) resulted in the micro-cavities serving as waveguides, and further enhanced the sensor characteristics. This results from the entrapment of more energy at the surface than when the micro-cavities are left unfilled (G. McHale, et al., "Theoretical mass sensitivity of Love wave and layer guided acoustic plate mode sensors," J. Appl. Phys 91(12), 9701-9710. (2002)). The boundaries of the microcavities which are normal surfaces to the SH wave present significant area for energy transfer to the lower density polystyrene in the micro-cavities, promoting energy trapping, which in turn brings up the energy to the surface, which would otherwise be lost to bulk waves. This is clearly evident from nodal displacements (data not shown).

The effects of micro-cavities and grooves on SAW propagation for sensor applications are illustrated using finite element methods. The device and sensor effects of filling these micro-cavities and grooves with a less dense and lower acoustic velocity material (polystyrene) were analyzed, and the data presented compare micro-cavity structured SAW sensors to traditional designs such as a plain delay path and an optimized waveguide coating. The micro-cavity structure data show significantly greater energy transmission than the other structures presented in this study. They also show moderate improvements in sensor sensitivity.

It was found that the microcavities in the delay path produce SH-SAW devices that are significantly superior to traditional SAW devices for sensing applications. These SH-SAW devices exhibit much lower energy loss and higher sensitivity when compared to all known methods such as introduction of gratings and guiding layers. Moreover, reliable finite element techniques were utilized to allow verification of the proposed designs with conclusive data.

Figure 14:
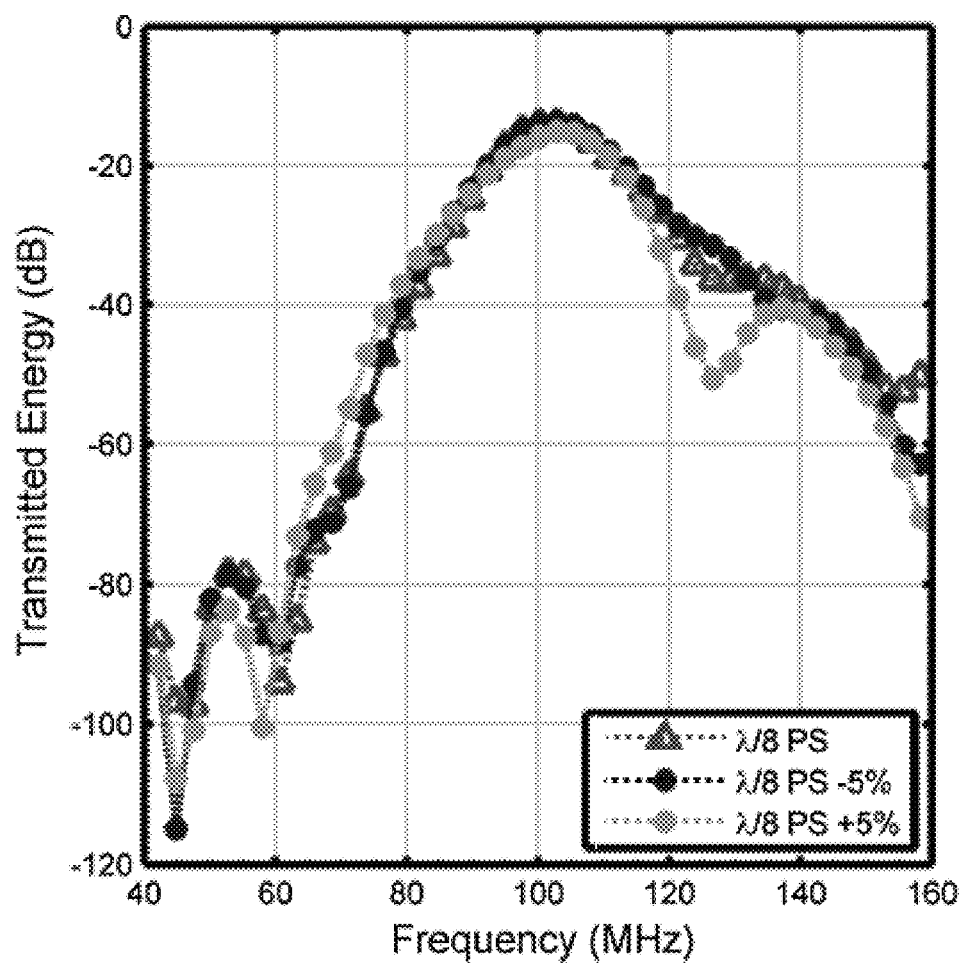
FIG. 14 is a graph showing the tolerances of the present devices, with micro-cavities enlarged and reduced by 5%. As seen, only significant changes are observed below 3 dB of the passband.
Figure 15:
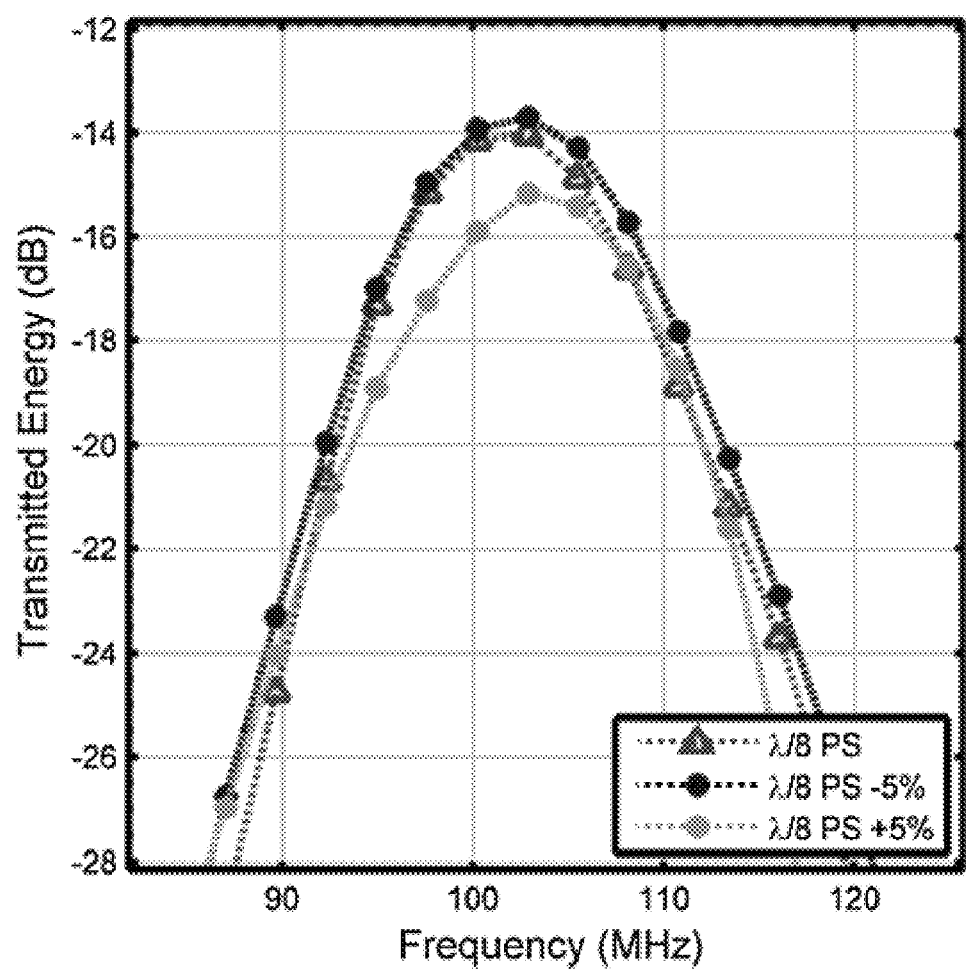
FIG. 15 is a graph showing the tolerances of the present devices, with micro-cavities enlarged and reduced by 5%. As seen, only significant changes are observed below 3 dB of the passband.

From the FE models, it is possible to test the tolerances necessary to fabricate the micro-cavity devices. A FEM study was performed to test tolerance and fabrication sensitivity, with the results indicating these devices may readily be fabricated in accordance with the results of this study. The optimized devices were studies with various modifications typical of common fabrication practices. Enlarging and reducing the micro-cavities by 5% exhibited minor impact of the devices through most of the device range, as seen in FIG. 14. Only significant changes are seen well below 3 dB of the passband. Closer inspection of the passband as shown in the right image shows the micro-cavities oversized to 5% greater than the design specification produces <2 dB decrease in transmitted energy, as seen in FIG. 15. From previous work correlating this finite element modeling tool and experimental work, this difference would even less substantial with a physical device.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a surface acoustic device, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A surface acoustic device, comprising
a piezoelectric substrate further comprising a first face and a second face;
a plurality of inter-digitated transducers disposed on the first face of the substrate;
an array comprising a plurality of micro-cavities disposed on the first face of the substrate;
wherein the micro-cavities are circular, triangular, pentagonal, or square when viewed from the first face of the substrate; and
wherein the micro-cavities are filled with a waveguide material, where the waveguide material has a lower density and lower acoustic velocity than the substrate.

2. The surface acoustic device of claim 1, wherein the micro-cavities have x-y dimensions selected from the group consisting of $\lambda/2 \times \lambda/2$, $\lambda/4 \times \lambda/4$, and $\lambda/8 \times \lambda/8$, wherein $\lambda$ is the wavelength of a wave propagated through the piezoelectric substrate.

3. The surface acoustic device of claim 2, wherein the micro-cavities have a z-dimension selected from the group consisting of $\lambda/2$, $\lambda/4$, and $\lambda/8$.

4. The surface acoustic device of claim 2, wherein the micro-cavities are $\lambda/2 \times \lambda/2 \times \lambda/8$ and filled with polystyrene.

5. The surface acoustic device of claim 1, wherein the substrate has the dimensions $40\lambda$ long, $5\lambda$ wide and $5\lambda$ deep, wherein $\lambda$ is the wavelength of a wave propagated through the piezoelectric substrate.

6. The surface acoustic device of claim 1, wherein the substrate is selected from the group consisting of quartz, R-plane sapphire, lithium niobate, lithium tantalate, gallium arsenide (GaAs), silicon carbide (SiC), langasite (LGS), zinc oxide (ZnO), aluminum nitride (AlN), lead zirconium titanate (PZT), polyvinylidene fluoride (PVdF), and 36° YX $LiTaO_3$.

7. The surface acoustic device of claim 1, wherein the inter-digitated transducers are $2\lambda$ long and $\lambda/4$ wide, wherein $\lambda$ is the wavelength of a wave propagated through the piezoelectric substrate.

8. The surface acoustic device of claim 7, wherein the inter-digitated transducers have a periodicity of 40 μm.

9. The surface acoustic device of claim 1, wherein the waveguide material filling the micro-cavities is polystyrene.

10. The surface acoustic device of claim 1, wherein twenty micro-cavities are disposed on the face of the substrate.

11. The surface acoustic device of claim 1, wherein the micro-cavities are disposed in an array of 4 rows of 5 micro-cavities.

12. The surface acoustic device of claim 1, wherein the device is adapted for use in a device selected from the group consisting of a sensor, a RF filter, a bandpass filter, an intermediate frequency filter, a voltage-controlled oscillator, an equalizer delay line, a multiple access delay line, a pressure transducer, and a convolver.

13. A method for increasing surface acoustic wave (SAW) device sensitivity comprising the steps of:
   providing a piezoelectric substrate with first face and a second face;
   etching an array comprising a plurality of micro-cavities on the first face of the substrate, wherein the micro-cavities are circular, triangular, pentagonal, or square when viewed from the first face of the substrate;
      wherein the micro-cavities are filled with a waveguide material, where the waveguide material has a lower density and lower acoustic velocity than the substrate; and
   adding a plurality of inter-digitated transducers disposed on the first face of the substrate.

14. The method of claim 13, wherein the micro-cavities have x-y dimensions selected from the group consisting of $\lambda/2 \times \lambda/2$, $\lambda/4 \times \lambda/4$, and $\lambda/8 \times \lambda/8$, wherein $\lambda$ is the wavelength of a wave propagated through the piezoelectric substrate.

15. The method of claim 13, wherein the micro-cavities have a z-dimension selected from the group consisting of $\lambda/2$, $\lambda/4$, and $\lambda/8$, wherein $\lambda$ is the wavelength of a wave propagated through the piezoelectric substrate.

16. The method of claim 13, wherein the waveguide material is polystyrene.

17. A method for decreasing surface acoustic wave (SAW) device power requirements comprising the steps of:
   providing a piezoelectric substrate with first face and a second face;
   etching an array comprising a plurality of micro-cavities on the first face of the substrate, wherein the micro-cavities are circular, triangular, pentagonal, or square when viewed from the first face of the substrate;
      wherein the micro-cavities are filled with a waveguide material, where the waveguide material has a lower density and lower acoustic velocity than the substrate; and
   adding a plurality of inter-digitated transducers disposed on the first face of the substrate.

18. The method of claim 17, wherein the micro-cavities have x-y dimensions selected from the group consisting of $\lambda/2 \times \lambda/2$, $\lambda/4 \times \lambda/4$, and $\lambda/8 \times \lambda/8$, wherein $\lambda$ is the wavelength of a wave propagated through the piezoelectric substrate.

19. The method of claim 17, wherein the micro-cavities have a z-dimension selected from the group consisting of $\lambda/2$, $\lambda/4$, and $\lambda/8$, wherein $\lambda$ is the wavelength of a wave propagated through the piezoelectric substrate.

20. The method of claim 17, wherein the waveguide material is polystyrene.

* * * * *